United States Patent [19]

Samuels

[11] Patent Number: 5,423,851

[45] Date of Patent: Jun. 13, 1995

[54] METHOD AND APPARATUS FOR AFFIXING AN ENDOLUMINAL DEVICE TO THE WALLS OF TUBULAR STRUCTURES WITHIN THE BODY

[76] Inventor: Shaun L. W. Samuels, 943 N. Figueroa Terr. #13, Los Angeles, Calif. 90012

[21] Appl. No.: 214,395

[22] Filed: Mar. 6, 1994

[51] Int. Cl.6 ............................................. A61M 5/00
[52] U.S. Cl. ....................................... 606/198; 623/1; 606/108
[58] Field of Search ........ 606/108, 152, 153, 191–195, 606/197, 198, 200; 623/1, 11, 12; 604/103–105, 8, 96; 128/898

[56] References Cited

U.S. PATENT DOCUMENTS

| | | |
|---|---|---|
| 3,334,629 | 8/1967 | Cohn . |
| 3,952,747 | 4/1976 | Kimmel . |
| 4,140,126 | 2/1979 | Choudhury . |
| 4,364,392 | 12/1982 | Strother et al. . |
| 4,638,803 | 1/1987 | Rand . |
| 4,641,653 | 2/1987 | Rockey . |
| 4,662,885 | 5/1987 | DiPisa . |
| 4,787,899 | 11/1988 | Lazarus . |
| 4,793,348 | 12/1988 | Palmaz . |
| 4,872,874 | 10/1989 | Taheri . |
| 5,053,008 | 10/1991 | Bajaj . |
| 5,104,399 | 8/1992 | Lazarus ................. 606/153 |
| 5,167,614 | 12/1992 | Tessmann et al. ........ 604/8 |
| 5,207,695 | 5/1993 | Trout, III ............... 606/153 |
| 5,234,448 | 8/1993 | Wholey et al. .......... 606/153 |

FOREIGN PATENT DOCUMENTS 0554082  8/1993  European Pat. Off. .............. 623/1

OTHER PUBLICATIONS

"Percutaneous Femoropopliteal Graft Placemente", Cragg & Dake, Radiology,1993, vol. 187, pp.643–648.
"Transfemoral Endovascular Aortic Graft Placement", Chuter et al. Journal of Vascular Surgery, Aug. 1993, vol. 18, No. 2, pp. 185–197.
"Transfemoral Intraluminal Graft Implantation for Abdominal Aortic Aneurysysms", Parodi et al., Annuls of Vascular Surgery, 1991, vol. 5, No. 6, pp. 491–499.

Primary Examiner—Stephen C. Pellegrino
Assistant Examiner—William W. Lewis
Attorney, Agent, or Firm—Rockey, Rifkin and Ryther

[57] ABSTRACT

A method and apparatus for affixing an endoluminal device to the walls of tubular structures within the body is disclosed which utilizes incremental inflation of a balloon cuff to deploy radially projecting barbs attached to the cuff within a plurality of recesses. At lower levels of cuff pressure, the engagement of the outer surface of the cuff with the tubular structure temporarily holds the device in place without tissue damage because the outer extremity of the barbs do not extend beyond the cuff's outer surface. If the device requires repositioning, then the cuff is easily deflated and moved to a new location and is again partially inflated. Once the location of the device has been found to be optimal, the cuff is fully inflated so as to deploy the barbs to permanently fix the device in place.

10 Claims, 3 Drawing Sheets

METHOD AND APPARATUS FOR AFFIXING AN ENDOLUMINAL DEVICE TO THE WALLS OF TUBULAR STRUCTURES WITHIN THE BODY

BACKGROUND AND SUMMARY OF THE INVENTION

The present invention relates generally to the field of surgical and interventional radiological techniques and more particularly to a method and apparatus for affixing an endoluminal device to the walls of tubular structures within the body. Examples of such structures are the biliary ductal system, the excretory system and blood vessels such as the aorta and the inferior vena cava.

One technique for permitting the repair of aortic aneurysms involves the utilization of a spring-like wound wire which provides the force to engage a plurality of anchoring pins to the vessel wall as exemplified in Choudbury, U.S. Pat. No. 4,140,126. Inherent in the operation of this device is the abrupt nature of its engagement with the wall of the healthy vessel and its capability of only being engaged or disengaged therefrom by the force of the spring-like would wire.

Additionally, a tubular graft could be implanted within a preselected blood vessel by inserting the graft endwise and axially through the blood vessel and secured into place therein by the engagement of surgical staple-like clips with the vessel wall as shown in Taheri, U.S. Pat. No. 4,872,874. The staple-like clips are engaged with the vessel wall due to the inflation of a balloon which is then removed from the vessel after engagement. Once the clips are engaged with the vessel, the graft is permanently inserted in the vessel and it cannot easily be moved without extensive damage to the surrounding vessel and tissue.

The main problem with securing endoluminal medical devices to a tubular wall is the risk of misplacement which can lead to catastrophic results such as the complete occlusion of the tube or possibly even the migration of the device to an undesired location. Additionally, damage to the tubular wall can occur when a device is being positioned within the tube if the apparatus used to secure the device employs exposed barbs or staples. Because of these problems, extensive fluoroscopic examination is required to ensure the correct placement of the device to minimize the risk of misplacement and tissue damage.

What is desired is a method and apparatus for repositionable replacement of an endoluminal medical device within the tubular structures of the body. The utilization of an inflatable balloon cuff provided with a plurality of small pockets or recesses arrayed on its outer surface in which a plurality of wall engagement barbs are secured satisfies this desire. When the cuff is not fully inflated, the barbs are disposed fully within the recesses and are prevented from engaging the tubular wall which precludes any possible damage to the walls.

At low levels of inflation of the cuff, only the smooth outer surface contacts the structure walls which allows the cuff to be moved and repositioned without damaging the surrounding tissue. In this way, the medical device can be positioned at the optimal location within the tubular structure. It can then be permanently affixed to the wall by fully inflating the cuff thereby causing the barbs to deploy and engage the wall.

Accordingly, it is an object of the present invention to provide a method and apparatus for affixing an endoluminal device to the walls of tubular structures within the body which satisfies the aforementioned desire. Also, it is an object of the present invention to provide a method in which medical devices can be affixed to tubular structure's walls without causing damage thereto and to prevent migration of the device after it has been affixed.

DETAILED DESCRIPTION OF A PREFERRED EMBODIMENT

Figure 1:
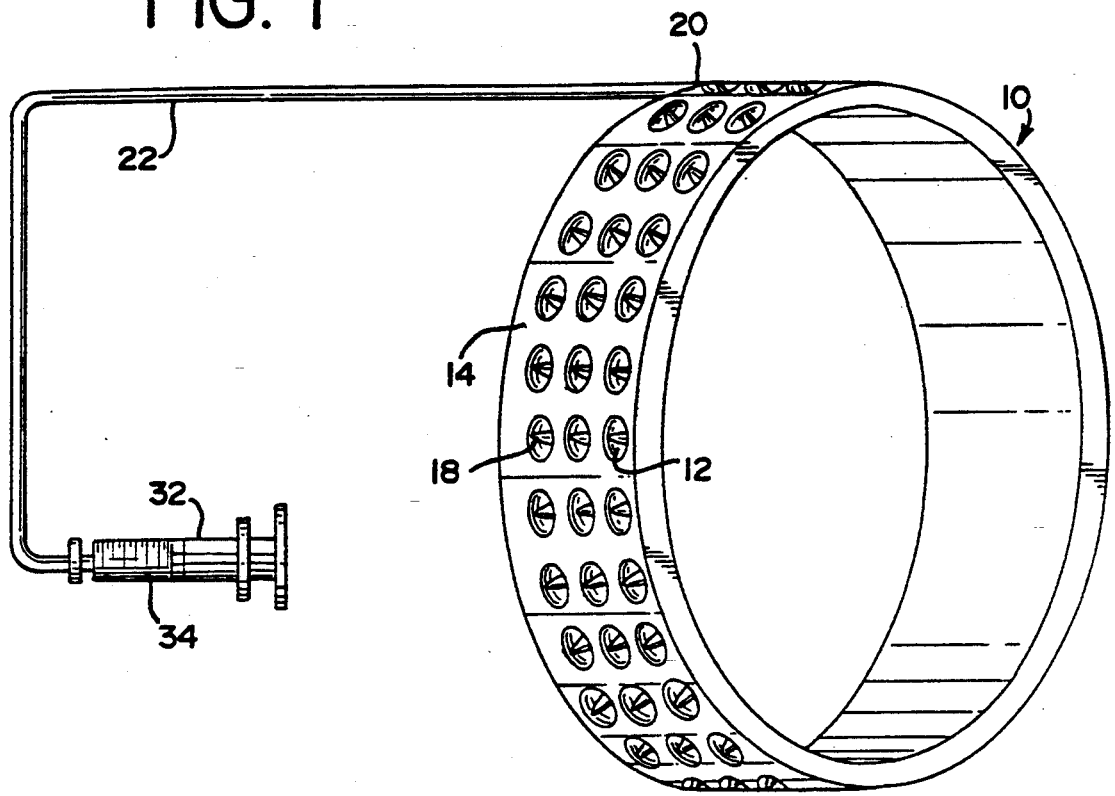
FIG. 1 is a pre-deployment perspective view of an apparatus for affixing an endoluminal medical device within the tubular structures of the body before the cuff has been inflated according to the present invention.
Figure 2:
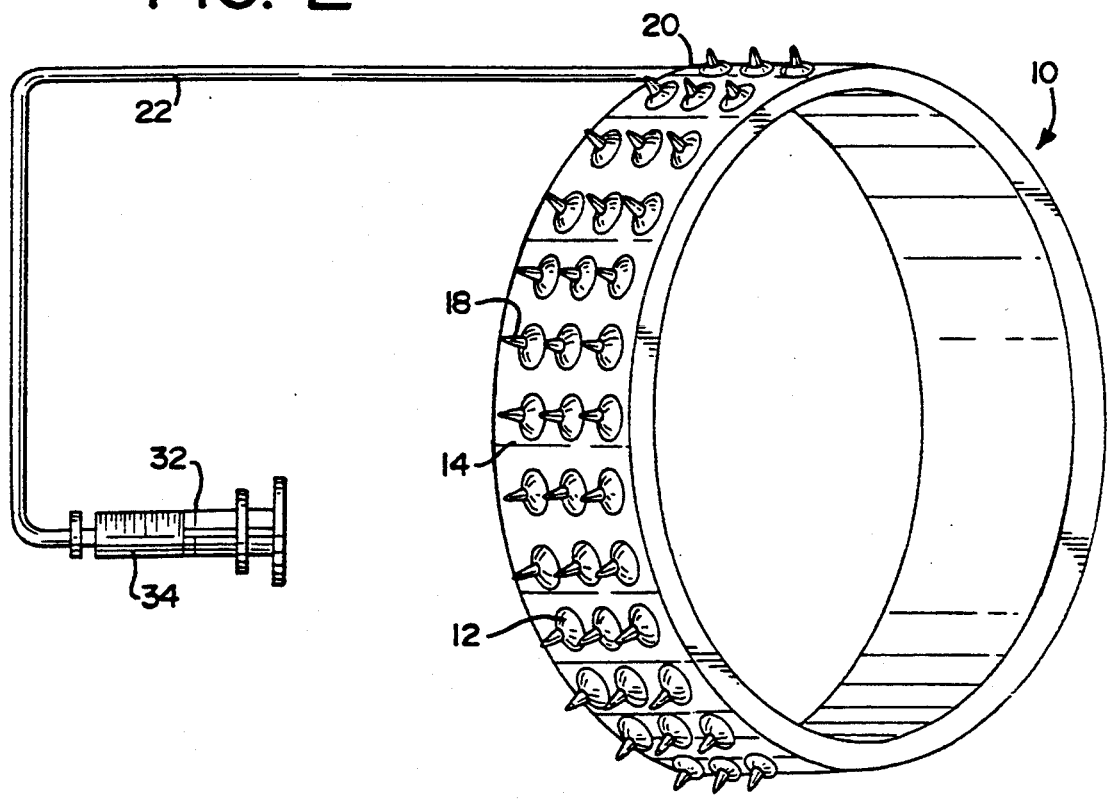
FIG. 2 is a post-deployment perspective view of an apparatus for affixing an endoluminal medical device which illustrates a fully inflated cuff showing the extension of the barbs from the recesses.

Referring to FIG. 1, a pre-deployment perspective view of an apparatus for affixing an endoluminal medical device within the tubular structures of the body before the cuff has been inflated is shown according to the present invention. The medical device (not shown) is secured to the inner surface of an inflatable balloon cuff 10 which includes a plurality of reinforced recesses 12 radially arrayed around its outer surface 14. The cuff 10 is manufactured to the appropriate diameter and width to fully support the medical device in the desired tubular structure of a patient.

Generally, the inflatable cuff 10 has a low profile when viewed down the axis of the center of the ring defining the cuff 10. Also, the inflatable cuff 10 and its outer surface 14 are preferably composed of a minimally distensible and slightly elastomeric polymeric plastic which is biologically inert. The material of the cuff 10 must be able to withstand high inflation pressures and must be of sufficient durability to provide for decades of effective use within the body.

The plurality of recesses 12 radially arrayed around cuff 10 also are preferably composed of a highly durable puncture resistant plastic which is biologically inert. As more precisely shown in FIGS. 3 and 4, the recesses 12 are dome-shaped when the cuff is fully inflated. Bonded to the reinforced recesses 12 are a plurality of individual barbs 18 which are composed either of carbonized steel or high impact plastic. When the cuff 10 is fully inflated, the recesses 12 pop out to allow the barbs 18 to engage the wall of a tubular structure within the body.

Figure 5:
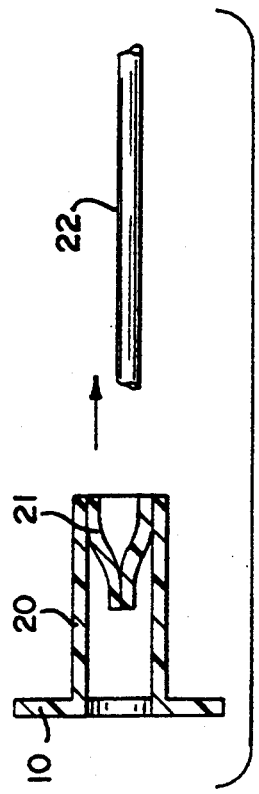
FIG. 5 is an enlarged cross-sectional view showing the inflation of the cuff by means of a duck bill valve.
Figure 6:
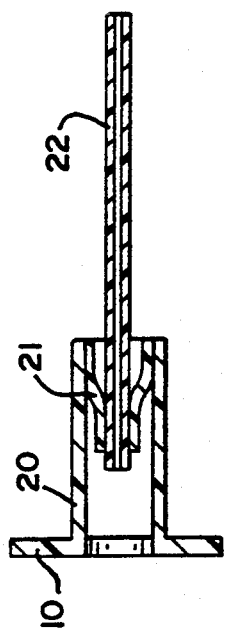
FIG. 6 is an enlarged cross-sectional view of the duck bill valve after the inflation tubing has been removed.

The cuff 10 is inflated and deflated by means of valve 20 (FIGS. 5 and 6) which is integral with a side of cuff 10. Preferably, valve 20 is a duck bill valve. Duck bill valve 20 is comprised of opposing leaflets 21 of a nonelastomeric, biologically inert material and is used in conjunction with inflation tubing 22. Tubing 22 is inserted into the valve 20 to separate the opposing leaflets 21 of the valve 20 when the cuff 10 is to be inflated or deflated. After the cuff 10 has been fully inflated, the tubing 22 is removed and the opposing leaflets 21 close to seal the inflated cuff 10.

Inflation material 34 is used to inflate the cuff 10 and preferably is a silicone-based rubber material. After the tubing has been removed and the valve has been sealed, the material 34 hardens over time to permanently affix the medical device to the tubular structure within the body.

It is within the scope of the present invention to utilize a pullaway detachable valve in place of duck bill valve 20. When a pullaway valve is used, the cuff 10 is inflated and deflated at low pressure to confirm its position and then is fully inflated at a higher pressure. After the inflation material 34 inside the cuff is slightly hardened, the operator of the device pulls on the inflation tubing to break connection with the cuff where the lumen is thinnest. Thus, the medical device is fully secured to the vessel wall.

In operation, the cuff 10 and the medical device are inserted into a patient by well know catheterization techniques. A non-exhaustive list of examples of applications of the present invention include: placing filters in the inferior vena cava, rigid tubes or stents in the vascular or biliary system to maintain the patency of the respective tubular structures and endoarterial grafts via a percutaneous approach. A single cuff is used to secure a vena cava filter to a vessel wall.

Figure 7:
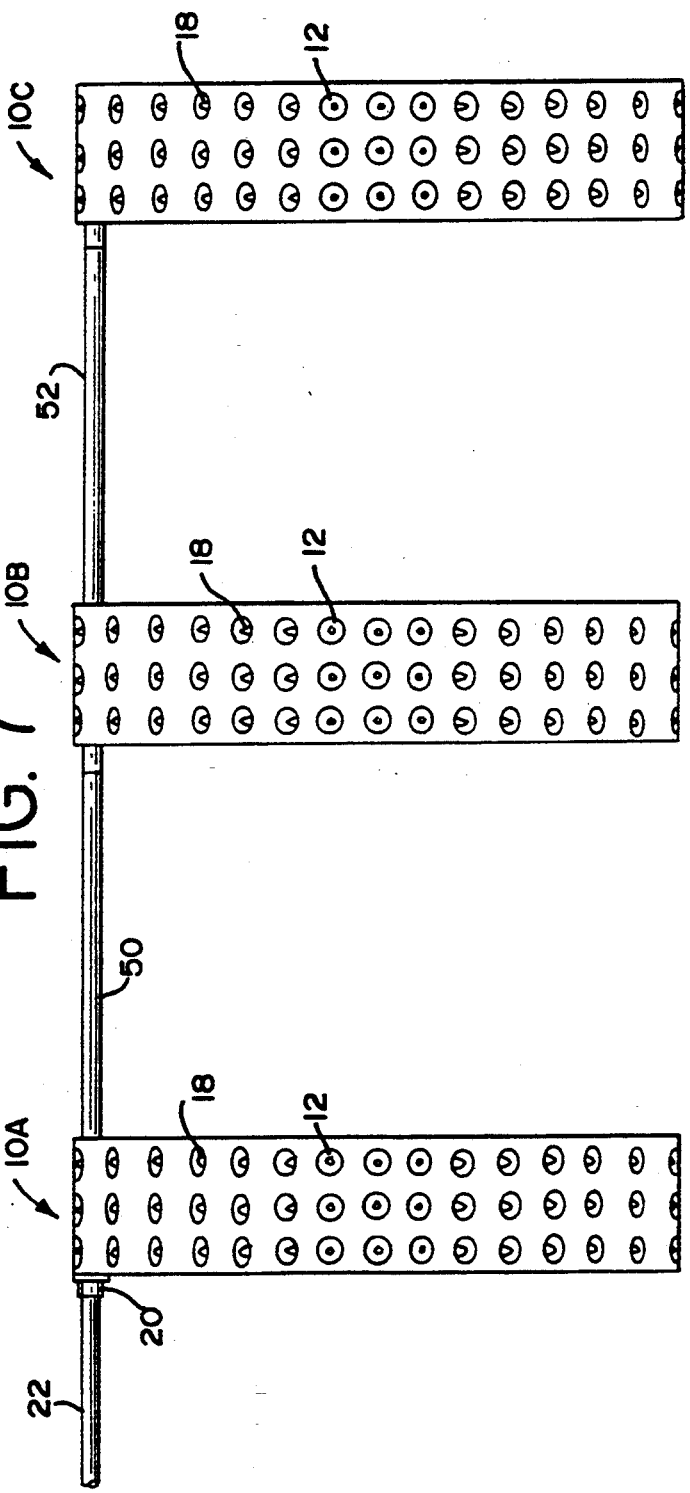
FIG. 7 is a side view of a ganged arrangement of three inflatable cuffs showing how each cuff is inflated by one valve.

Referring to FIG. 7, a side view of a ganged arrangement of three inflatable cuffs is shown. A gang of inflatable cuffs preferably is used to affix long tubes, stents or endoarterial grafts which require more support due to their length. Cuff 10A includes valve 20 and inflation tubing 22 as described before and is connected to cuff 10B via spine 50, cuff 10B being connected to cuff 10C via spine 52. The spines 50 and 52 interconnect the cuffs 10A-10C such that all three can be simultaneously inflated and deflated with inflation material 34.

The first step in using the present invention is to secure the medical device to the inflatable cuff 10 by means of biologically inert adhesives, the combination being delivered to the appropriate location in the tubular structure by means of well known catheterization techniques. For affixing an endoluminal graft, the graft could be manually positioned in the desired location. The inflatable cuff is then inserted inside the graft and is fully inflated causing the barbs to extend through the graft itself into the vessel wall. Because no adhesive bonding is used, the risk of separation between the graft and cuff due to the different elastomeric qualities of each material is minimized.

Figure 3:
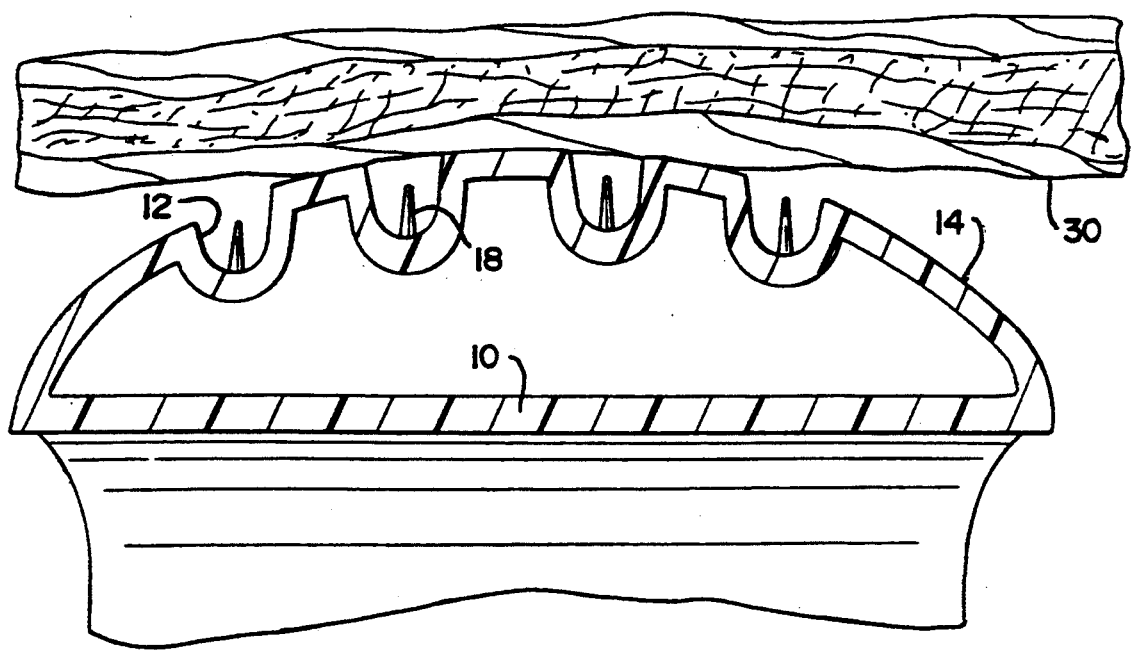
FIG. 3 is a sectional view of a partially inflated cuff showing the engagement of the outer surface of the cuff with the structure's wall while the barbs are inside the recesses.
Figure 4:
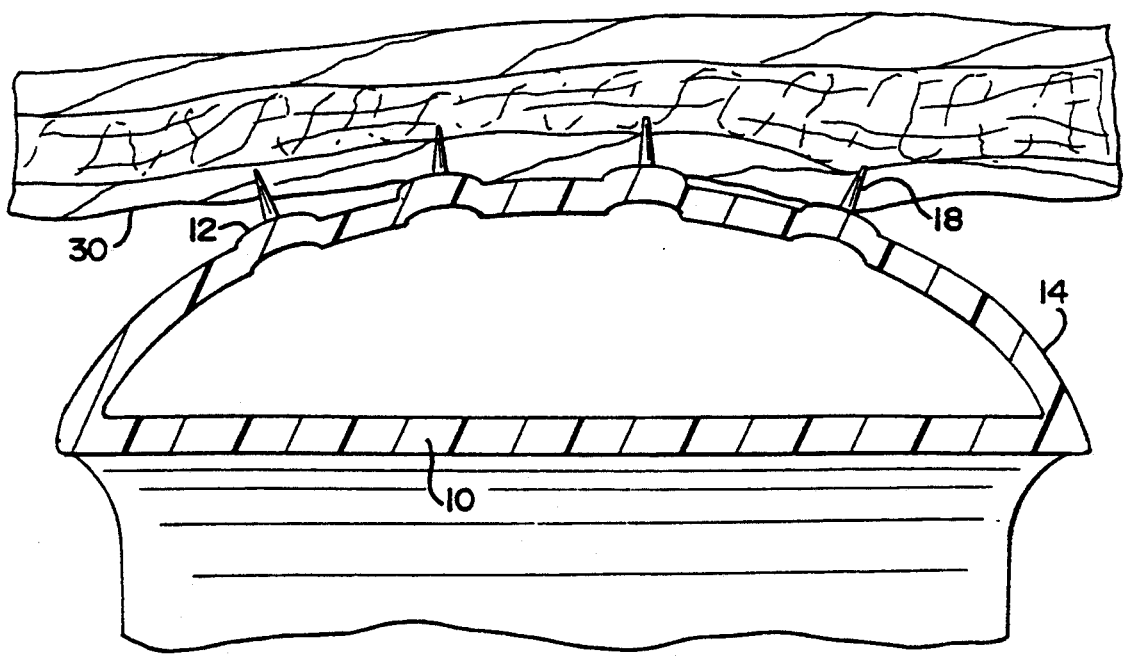
FIG. 4 is a sectional view of the inflatable cuff showing the engagement of the barbs with the structure's wall when the cuff is fully inflated.

Referring to FIG. 3, a sectional view of a partially inflated inflatable cuff 10 is illustrated showing the engagement of its outer surface 14 with the structure's wall when the barbs 18 are inside the recesses. FIG. 3 highlights a unique feature of the present invention which is its capability of being optimally positioned within the tubular structure in the body without causing damage to the surrounding tissue. Specifically, when the balloon cuff 10 is at lower levels of inflation and after it has been inserted into the body by catheterization, the outer surface 14 holds the cuff 10 in place against the wall 30 so that it can be determined whether the positioning of the medical device and the cuff 10 is optimal.

If the position is found to be optimal, then the cuff 10 is fully inflated so that the barbs 18 rigidly engage with the wall 30 to permanently hold the medical device in place. On the other hand, if the position is not optimal, then the cuff 10 can be deflated and moved to the optimal position without harming or damaging the surrounding tissue.

Referring back to FIG. 1, the cuff 10 is inflated by means of an inflation syringe 32 with an inflation material 34 which is preferably a silicone-based liquid when injected into the cuff which hardens over time. After the inflation material 34 hardens, the medical device held within the inflatable cuff 10 is permanently attached to the tubular cavity within the body. Typically, the inflation syringe 32 is mounted in a screw-feed pressure generating device provided with a manometer in order to properly gauge inflation pressures accurately.

The present invention can be constructed in many different sizes and shapes. The only criterion which must be met is that the cuff 10 must be of an appropriate width and diameter so that the medical device to be used can be fully supported within the tubular structure by the cuff 10. Not only can the invention be practiced in small structures such as the arterial system, but also, the medical devices can be affixed within much larger structures such as in the excretory system.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of affixing an endoluminal medical device to the walls of a tubular structure within the human body comprising the steps of:
   (a) securing the medical device to an inflatable cuff having an outer surface and a plurality of recesses disposed around said outer surface, said cuff including a plurality of radially extending barbs attached to said cuff within said recesses such that the outer extremity of said barbs do not extend beyond the outer surface of said cuff when said cuff is deflated;
   (b) introducing said cuff and medical device into said tubular structure;
   (c) partially inflating said cuff with inflation material so that only its outer surface, but not said barbs, engages said tubular structure to temporarily hold said cuff and medical device in place while it is determined whether the location of engagement is satisfactory; and
   (d) fully inflating said cuff so as to extend said barbs into engagement with said wall of said tubular structure to permanently engage said tubular structure.

2. The method of claim 1 further including the step of deflating said cuff before it is fully inflated to disengage said outer surface of said cuff from said chosen circumference of said tubular structure's wall allowing engagement with a different portion of said wall of said tubular structure.

3. The method of claim 2 wherein said inflation material is a silicone-based liquid which hardens over time into a vulcanized rubber material.

4. The method of claim 3 wherein said step (a) includes the sub-step of providing an inflatable cuff having an appropriate diameter and width suitable for securing said cuff and medical device within a tubular structure of varying dimensions.

5. The method of claim 1 wherein said step (b) is accomplished by means of catheterization.

6. An apparatus for affixing an endoluminal device to the walls of tubular structures with in the body comprising:
   a) an inflatable cuff having an outer surface and a plurality of recesses radially arrayed around said outer surface;
   b) a valve integral with said cuff to permit inflation and deflation;
   c) a plurality of radially extending barbs attached to said cuff within said recesses such that when said cuff is deflated, the outer extremities of said barbs do not extend beyond the outer surface of said cuff; and
   d) means for inflating and deflating said cuff with an inflation material to extend said barbs beyond the outer surface of said cuff to engage the walls of said tubular structure,
   whereby partial inflation of said cuff permits its engagement with the wall of said tubular structure to temporarily hold said cuff and said device in place, deflation of said cuff disengages said outer surface to allow repositioning and full inflation permanently attaches said cuff to the walls by extending said barbs into said tubular structure.

7. The apparatus of claim 6 wherein said inflation material is a silicone-based liquid which hardens over time.

8. The apparatus of claim 6 wherein said inflatable cuff is composed of an elastomeric polymeric plastic which is biologically inert.

9. The apparatus of claim 6 wherein said barbs are composed of carbonized steel.

10. The apparatus of claim 6 wherein said barbs are composed of a high impact plastic.

* * * * *